United States Statutory Invention Registration [19]

[11] Reg. Number: H223

Seiders et al.

[43] Published: Mar. 3, 1987

[54] DECONTAMINATION OF MUSTARD GAS WITH SUPEROXIDE

[75] Inventors: Reginald P. Seiders, Chapel Hill, N.C.; J. Richard Ward, Bel Air, Md.

[73] Assignee: The United States of America as represented by the Secretary of the Army, Washington, D.C.

[21] Appl. No.: 870,215

[22] Filed: May 22, 1986

[51] Int. Cl.[4] ..... C09B 47/04; A01N 59/24; A61K 33/00

[52] U.S. Cl. ..... 422/1; 8/661; 568/56; 568/60; 427/331; 424/127; 424/129

*Primary Examiner*—John F. Terapane
*Assistant Examiner*—Susan Wolffe
*Attorney, Agent, or Firm*—Anthony T. Lane; Harold H. Card, Jr.; Edward F. Costigan

[57] ABSTRACT

Articles or structures can be treated to convert mustard gas to divinylsulfide by coating on said articles or structures a composition containing a transition metal complex of a tetrasulfonated or tetraamino phthalocyanine.

18 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

DECONTAMINATION OF MUSTARD GAS WITH SUPEROXIDE

GOVERNMENT RIGHTS

The invention described herein may be manufactured, used and licensed by the Government for Governmental purposes without the payment to us of any royalties thereon.

BACKGROUND OF THE INVENTION

1. Field of Invention

This invention relates to a means for decontaminating objects that have been or are expected to be exposed to mustard gas [bis-(2-chloro-ethyl)sulfide].

2. Prior Art

Mustard gas is a well known poison gas which was used extensively during World War I. Although it has been banned from use at any time, certain uses have been documented. There is a need therefore, in the interests of preparedness, for a decontaminant which is readily available during wartime and especially on the battlefield.

The present standard decontaminating means is a solution of DS-2 which is composed of, on a weight basis, 70% diethylenetriamine, 28% 2-methoxyethanol and 2% sodium hydroxide. DS-2 reacts rapidly with mustard gas via proton abstraction leading to dehydrochlorination of the mustard gas to form divinylsulfide. DS-2, however, is not widely applicable since it is corrosive to metals and incompatible with a number of polymers, e.g. Laxan, polyvinyl chloride, cellulose acetate, acrylic, Mylar. Furthermore, the ingredients of DS-2 are generally unavailable in military theaters of operation, necessitating procuring them and supplying them through the entire logistic chain, an expensive and cumbersome procedure.

There is thus a need for decontaminants that are available on the battlefield and are compatible with military equipment.

SUMMARY OF INVENTION

This invention relates to a method of decontaminating articles and/or structures contaminated with or expected to be contaminated with mustard gas by treating the articles and/or structures with a transition metal complex of a tetrasulfonated or tetraamino phthalocyanine catalyst which binds oxygen from the air and converts the oxygen to superoxide. The superoxide dehydrochlorinates the mustard gas to divinylsulfide.

Typical of such catalysts are cobalt(II) tetrasulfonated phthalocyanine (CoTSPC) and cobalt(II) tetraamino phthalocyanine (CoTAPC), preferred is CoTSPC.

The invention can be carried out by forming articles and/or structures that are self-decontaminating by coating, e.g. buildings, tanks, automobiles and the like with paint having incorporated therein a decontaminating effective amount of a transition metal complex of a tetrasulfonated or tetraamino phthalocyanine catalyst.

This invention also contemplates compositions containing decontaminating effective amounts of the catalyst with a carrier.

As used herein "transition metals" means nickel, cobalt or iron with cobalt(II) preferred.

DETAILED DESCRIPTION

This invention provides a means to bind oxygen from air, convert it to superoxide and treat articles and/or structures contaminated with mustard gas or expected to be contaminated with mustard gas with the superoxide to dehydrochlorinate the mustard gas and convert it to primarily divinylchloride.

Articles and/or structures amenable to such treatment are buildings, military vehicles, artillary weapons, tents, clothes and the like. The treatment in its most preferred form is prophylactic in character since the articles and/or structures treated are painted, coated or dyed with a composition containing a transition metal complex of a phthalocyanine substituted with sulfonic groups or amino groups.

The preferred transition metal is cobalt(II) and the preferred phthalocyanine is the tetrasulfonated complex with cobalt(II).

The invention will be described in its preferred aspects.

Cobalt(II) tetrasulfonated phthalocyanine (CoTSPC) is prepared by methods well documented in the art, e.g. Weber et al., Inorganic Chemistry, 4, 469 (1965). The compound is most useful when incorporated into coating compositions such as paints, polymers and dyes.

The paints and polymers are coated onto articles or structures which are possible targets of mustard gas attacks, forming a self-decontaminating coating thereon.

The CoTSPC can also be mixed with fabric-dye compositions then dyed onto the fabric, forming self-decontaminating fabrics used for clothes, tents, military camouflage and the like.

The amount of CoTSPC used in the coating or dyeing compositions is critical only to the extent that there cannot be an amount used that will deleteriously affect the properties of the coating or dyeing composition or an amount used which will be so high as to cause the catalyst to aggregate and diminish its effectiveness as an oxygen binder. Generally, on a weight basis, CoTSPC is substituted for from about 0.5 to 2.0 percent of the pigment in paints, polymers or dyes.

For example, when used in military camouflage paints with alkyl paint pigments, the amount of CoTSPC that can be used is limited by its effect on other desirable properties of the paint, particularly camouflage. As the thin film of paint is drying, the large surface area facilitates oxygenation of the CoTSPC. The oxygen in the CoTSPC is converted to superoxide $O_2^-$ and results in a self-decontaminating paint film which forms during the typical 24 hour curing time of the paint.

The paint detoxifies the mustard gas by absorbing it and dehydrochlorinating it to form divinyl sulfide.

After the absorbed mustard gas is dehydrochlorinated in the paint by the superoxide formed by the oxygenated CoTSPC, a period of 12 to 24 hours is needed for the decomposition products of the mustard gas, primarily divinylsulfide, to desorb from the paint and for re-oxygenation of the catalyst to occur. Since it is not expected that paint, for example, will be saturated with mustard gas, but that only spots will be contaminated, the painted surface will retain its self-decontaminating capacity during the time the spent CoTSPC is regenerated.

Similarly, when used as a replacement for part of the pigment in polymeric coating agents or fabric dyes, the amount of CoTSPC used is limited by its effect on other properties of the polymer or dye.

When mustard gas is absorbed onto a coating such as paint, and it is not destroyed by the coating or subsequent decontamination processes, it gradually desorbs, creating a residual vapor hazard.

This invention prevents such a hazard from occurring. In addition, the active agent of this invention is not corrosive to, e.g., metal or plastics, and it uses a readily available material, oxygen, from air.

In order to demonstrate that a superoxide dehydrochlorinates mustard gas or similar materials, potassium superoxide ($KO_2$) was mixed with 2-chloroethylsulfide (CEES) and the NMR (nuclear magnetic resonance) monitored for the presence of vinyl protons. Solvents transparent in the NMR where the vinyl protons appeared were used. The following illustrates the experiment.

An 0.86 M solution of CEES in dimethyl formamide (DMF) was formed by dissolving 1.1 ml of CEES in 10 ml DMF. 0.79 gm of $KO_2$ (10.7 m moles) was added to the solution and the reaction mixture (yellow colored) was stirred at room temperature (about 20° C. to 25° C.). After about one hour, the yellow color of the solution faded and a fine white precipitate of KCl appeared. A sample of the solution was decanted and the proton NMR spectrum examined revealing the presence of vinyl protons. The presence of the vinyl protons indicated the formation of ethylvinylsulfide. This was confirmed by comparison of the spectrum with that of the authentic material.

This experiment showed that CEES can eliminate HCl from only one side of the molecule, whereas mustard gas can eliminate HCl from either side of the sulfur, thus, the reactivity of the mustard gas is inherently greater than that of CEES.

Potassium superoxide ($KO_2$) does not use atmosphere oxygen but is used to demonstrate the reactivity of superoxides because it is a convenient and clear source of $O_2^-$.

CoTSPC reversibly binds atmospheric oxygen and has been found by Zwart et al., J. Molec. Cat., 5, 51 (1979) to form a $Co(III)O_2^-$ complex and thus should act as a superoxide and dehydrochlorinate mustard gas.

We claim:

1. A method of preventing contamination or decontaminating articles or structures in need of such treatment which comprises treating said articles or structures with a decontaminating or prevention of contamination effective amount of a catalyst which binds atmospheric oxygen and converts it to a superoxide.

2. The method of claim 1 wherein the catalyst is a transition metal complex of a phthalocyanine.

3. The method of claim 1 wherein the catalyst is Co(II) tetrasulfonated phthalocyanine.

4. The method of claim 1 wherein the catalyst is Co(II) tetraamino phthalocyanine.

5. The method of claim 1 wherein said articles or structures are treated by coating them with a paint containing an effective amount of said catalyst.

6. The method of claim 5 wherein the catalyst is Co(II) tetrasulfonated phthalocyanine.

7. The method of claim 5 wherein the catalyst is Co(II) tetraamino phthalocyanine.

8. The method of claim 1 wherein the article or structure fabric and the treatment is dyeing the fabric with a dye composition containing an effective amount of catalyst.

9. The method of claim 8 wherein the catalyst is Co(II) tetraamino phthalocyanine.

10. The method of claim 8 wherein the catalyst is Co(II) tetrasulfonated phthalocyanine.

11. A decontaminating composition for dehydrochlorinating mustard gas comprising an effective decontamination amount of an atmospheric oxygen binding catalyst and a carrier.

12. A composition of claim 11 wherein the carrier is a paint composition and the catalyst is Co(II) tetrasulfonated phthalocyanine.

13. A composition of claim 11 wherein the carrier is a paint composition and the catalyst is Co(II) tetraamino phthalocyanine.

14. A composition of claim 11 wherein the carrier is a polymer film former and the catalyst is Co(II) tetrasulfonated phthalocyanine.

15. A composition of claim 11 wherein the carrier is a polymer film former and the catalyst is Co(II) tetraamino phthalocyanine.

16. A composition of claim 11 wherein the carrier is a fabric dye and the catalyst is Co(II) tetrasulfonated phthalocyanine.

17. A composition of claim 11 wherein the carrier is a fabric dye and the catalyst is Co(II) tetraamino phthalocyanine.

18. A method of making an article or structure self-decontaminating which comprises coating said article or structure with an effective amount of the composition of claim 12.

* * * * *